United States Patent [19]

Snapka et al.

[11] Patent Number: 5,071,775

[45] Date of Patent: Dec. 10, 1991

[54] INDIRECT LABELING METHOD FOR POST-SEPARATION DETECTION OF CHEMICAL COMPOUNDS

[75] Inventors: Robert M. Snapka, Columbus, Ohio; Kwan S. Kwok, Newton, Mass.; John A. Bernard, Jr., Needham Heights, Mass.; Otto R. Harling, Hingham, Mass.; Alexander Varshavsky, Boston, Mass.

[73] Assignee: Massachusetts Institute of Technology, Cambridge, Mass.

[21] Appl. No.: 896,149

[22] Filed: Aug. 13, 1986

[51] Int. Cl.$^5$ ............... G01N 33/534; G01N 33/566; G01N 33/567; C12Q 1/68

[52] U.S. Cl. .................... 436/545; 436/501; 436/504; 436/518; 436/538; 436/542; 436/56; 436/57; 435/6; 935/78

[58] Field of Search ............... 536/26, 27, 28, 29; 436/504, 545, 501, 518, 76, 81, 538, 82, 84, 56, 57; 423/249; 435/6; 935/78; 424/1.1

[56] References Cited

U.S. PATENT DOCUMENTS

| | | | |
|---|---|---|---|
| 3,576,994 | 5/1971 | Parks et al. | 424/1.1 |
| 4,205,952 | 6/1980 | Cais | 436/518 |
| 4,587,223 | 5/1986 | Sioni et al. | 436/501 |

OTHER PUBLICATIONS

Kocsis, E. et al., "Determination of Manganese in Blood by Neutron Activation Analysis", Chem. Abs. 95:57519s, 1981.

CRC Handbook of Chemistry and Physics, pp. 13–13, 13–14, 13–16, 1981–1982.

Norhelm, G. and Steinnes, E., "Determination of Protein-Bound Trace Elements in Biological Material by Gel Filtration and Neutron Activation Analysis", *Analytical Chemistry*, vol. 47, No. 9, pp. 1688–1690, Aug. 1975.

Diels, L. et al., "An RNA Sequencing Method Based on a Two-Dimensional Combination of Gel Electrophoresis and Thin-Layer Chromatography", Chem. Abs., 93:3414u, 1980.

*Primary Examiner*—Esther L. Kepplinger
*Assistant Examiner*—Janelle Graeter
*Attorney, Agent, or Firm*—Paul J. Cook

[57] ABSTRACT

A sensitive and general method of post-separation detection and quantification of chemical compounds is described. The method involves separation of unlabeled compounds by chromatography, electrophoresis or other means and selective binding of the separated compounds to ligands containing highly neutron-activatable elements, followed by neutron irradiation. The neutron-activatable elements are converted to their radiation-emitting isotopes by neutron absorption, and detection is done by autoradiography, fluorography or other means of radiation detection. The theoretical sensitivity of the method is in the attomole ($10^{-18}$ mole) range.

15 Claims, No Drawings

INDIRECT LABELING METHOD FOR POST-SEPARATION DETECTION OF CHEMICAL COMPOUNDS

The Government has rights in this invention pursuant to Grant Number NIH-5-RO1-CA33297-02 awarded by the Department of Health and Human Services.

FIELD OF THE INVENTION

The present invention relates to a method for post-separation, detection and quantification of chemical compounds.

BACKGROUND OF THE INVENTION

Radioactive labeling is one of the most sensitive analytical strategies for the detection of chemical compounds. However, applications of this approach in biochemistry are often subject to significant constraints. In vivo radiolabeling may be complicated by radiation damage to cells and by competition from intracellular pools of precursors. In vitro radiolabeling, while producing much higher specific radioactivities, often results in undesired chemical modification of the original compounds which may greatly complicate their separation and identification unless radiolabeling is carried out after separation of the original compounds.

Schmeiser et al have suggested that one general method for such post-separation labeling is the neutron activation analysis, Angew Chem., 65:490-491 (1953). This technique is based upon selective induction of radioactivity in some of the atoms of the elements making up the sample by irradiating the sample with neutrons and then measuring the radioactivity of newly formed unstable isotopes in the sample. In the "direct labeling" method of post-separation detection via neutron activation, one or more of the elements present in the separated compounds of interest are directly converted into their radioactive isotopes by irradiation with neutrons in situ. In one early application of this approach, phosphorus ($^{31}$P)-containing compounds such as phospholipids, have been detected after their separation by paper chromatography using neutron activation to convert $^{31}$P into radioattive $^{32}$P, Strickland et al, *Arch. Biochem. Biophys.* 88: 344-348 (1960); Nahayama et al, *Acta. Chem. Scand.* 15: 1595-1603 (1961); Blomstrand et al, *J. Neurochem.* 8: 230-233 (1961); Robinson, *Canad. J. Biochem.* 9: 21-34 (1964) and Johnson et al, *J. Res.* 6: 435-427. However, this technique has limited applicability and sensitivity primarily due to the low neutron activation cross-section of phosphorus. It would be desirable to provide a labeling technique which is much more sensitive and more generally applicable than the direct labeling method.

SUMMARY OF THE INVENTION

In accordance with this invention, there is provided a method for quantifying a constituent of a substrate composition. An element having a large neutron absorption cross-section is bound either directly or indirectly through a ligand to the substrate composition either prior to or subsequent to separating the substrate composition into its constituent parts. The element must be capable of being converted by neutron absorption to an isotope that emits detectable radiation. The substrate separated into its constituents then is irradiated to produce the radiation-emiting isotope. Thereafter, the presence of at least one constituent of the substrate is detected or quantified by detecting or measuring the radiation emitted by the radioisotope bound to the constituent, if any.

DETAILED DESCRIPTION

The substrate composition to be analyzed according to the techniques of the present invention can be derived from any one of a large variety of sources. All that is necessary is that at least one component of interest in the substrate composition be capable of being coupled (either directly or through a molecular bridge) to an element that is neutron activatable. Representative suitable substrate compositions include compositions containing biologically active molecules such as antigens, antibodies, enzymes and other proteins, nucleic acids, lipids, polysaccharides, polymers of nonbiological origin and low molecular weight compounds for which selectively binding activatable ligands can be designed. Even isotopes of elements which are not highly neutron activatable are useful in the process of this invention so long as the isotope is activatable to produce an isotope that is radiodetectable. The process of this invention permits labeling a wide variety of substrate constituents since a wide variety of labeling elements having different chemical activity can be utilized. In addition, the present invention can provide greater sensitivity than the prior art direct labeling process since elements having large neutron adsorption cross-sections can be utilized which are highly activatable and are more easily detectable than $^{32}$P.

The molecular species to be detected and quantitated are separated from each other prior to irradiation. This separation is preferably a physical separation and may be performed by methods known in the art such as chromatography, electrophoresis or any other conventional physio-chemical means. An important aspect of the present invention is that molecules to be detected are not irradiated until after the separation. Chromatographic techniques involve the process of selective retardation of one or more components of a fluid solution as the fluid uniformly moves through a column of finely divided substance or capillary passageways. The retardation results from the distribution of the components of the mixture between one or more stationary phases and the bulk fluid, as this fluid moves through or over the surface of the stationary phases. The term "solution" in the above definition implies that the distribution process occurs at the molecular level. Under known electrophoresis techniques, colloidal particles or macromolecules with a net electric charge migrate in a medium such as a gel under the influence of an electric field.

It is preferred that the support material or matrices used in the separation step comprise elements which, when irradiated, have a half life less than both phosphorus, if present, and the metal cation bound to the molecule. The common support matrices for chromatography and gel electrophoresis are composed of carbon, hydrogen, oxygen and nitrogen, all elements which are not converted by neutrons into isotopes that interfere with the post-separation detection of substrates of interest by the indirect labeling method described above. When the chromatography technique is used, the separated portions of molecules according to type are in the form of a chromatogram. A chromatogram is a pattern formed by zones of separated substances. When the electrophoretic technique is used, the separated molecules are separated as zones or spots in gels. In either of the above cases, the support matrix after separation comprises materials of separate and distinct compositions according to a type of molecule. Each of the separate electrophoretic or chromatographic spots often consists essentially of one type of molecule. A neutron activatable element can be bound to the above molecule either prior to or subsequent to separating the molecules.

Next, at least one of the separated molecular species is irradiated. Typically, more than one or all of the separated portions within the matrix material are irradiated in a batch operation. During irradiation of the matrix support which includes the separated molecular species, the neutron activatable element bound to the molecule of interest absorbs neutrons to form a radio-emitting isotope. Several elements such as dysprosium and europium have particularly large neutron absorbing cross-sections and thus are more susceptible to being converted into a radio-emitting isotope as compared to phosphorus. This reduces the time needed for irradiation and/or the dose of irradiation required. The neutron irradiation may be performed by methods known in the art. Elements of smaller neutron absorbing cross-sections may also be useful in the indirect labeling method, especially if neutron irradiation converts them into unstable isotopes with high-energy decay patterns.

The extent of neutron activation of a given element depends upon three factors: the neutron flux used, the neutron absorption cross-section of the isotope (the target size of the nucleus as experienced by neutrons expressed in Barns; 1 Barn = $10^{-24}$cm$^2$), and the time during which the parent isotope is irradiated. The neutron flux used and the absorption cross-section of the isotope determine the ultimate attainable activation, known as the saturation value. This value is approached asymptotically with irradiation time and is only reached after irradiation for an infinite number of half-lives. However, irradiation for one half-life gives 50% saturation and irradiation for four half-lives gives 94% saturation.

To obtain desirable high levels of detection, the ratio of signal to background radiation resulting from activated elements in the support matrix should be maintained at a suitable level. Signal to background is a limiting factor in the detection of molecules wherein highly activatable element is bound to the molecule. The background is due to radiation from activated elements in the support matrix. Trace elements, especially metals can contribute to this background. The signal to background ratio can be improved in a number of ways. The first method is use of filters in autoradiography. After irradiation, the celluloses and agaroses employed give off most of their beta-radiation in the tritium and $^{14}$C energy range and very little in the $^{32}$P range or in the range of the radio-emitting element utilized. Thus, most of the beta-ray background can be screened out with thin aluminum or plastic sheets which are placed between the sample and the film. A second method of improving the signal to background ratio is the use of decay time. Many of the trace elements which activate in the support matrix will decay away in minutes, hours or days. An example is $^{24}$Na which has a much shorter half-life than phosphorus. Therefore, this element is usually not detectable in samples after a two day "cooling off" period following the end of irradiation.

Two other methods of improving signal to noise ratio are adjustment of irradiation time and special washing and preparation of support matrices. Since each element activates as a function of its half-life, the irradiation can be adjusted to maximize signal to background. Acceptable results may be achieved with commercial agarose and cellulose-derived thin layer chromatography (TLC) plates without special preparation. Treatment with chelators alone will significantly reduce the background of support matrices such as those used herein.

It should also be noted that the sensitivity of the method described here is dependent not only on the purity of the support matrices but on utilizing support materials that have very high capacities for their weights to permit efficient separations of molecules on a support matrix of low relative mass. Since no material is absolutely free of trace elements which may activate, no material is exposed to a high flux neutron beam without some radioactivity being produced. Thus, the background radioactivity from the support matrix can be reduced by reducing its mass. Handling of thin layers and membranes may be conveniently performed by attaching them to plastic sheets which are removed and discarded after irradiation.

The separated molecules are combined with the highly activatable element present as a part of a selectively binding ligand and the irradiated element detected to quantify the molecules. The cations of transition metals as well as the lanthanides and actinides, for example, have been used as electron dense stains for electron microscopy. Biomolecules such as nucleic acids and proteins tend to directly chelate these metals tightly, largely due to phosphate and carboxyl groups. Alternatively, when the molecule of interest does not contain molecular groups capable of directly binding the metal cation, the metal cation first is bound to a molecule capable of selectively binding to the molecule of interest such as an antigen for an antibody of interest or a substrate for an enzyme of interest. Several of these metals have very large neutron absorption cross-sections and the corresponding radioactive isotopes have relatively short half-lives. Typical elements of this type include manganese, dysprosium and europium. Dysprosium-165 ($^{165}$Dy) $\beta$-decays well within the $^{32}$P energy range. Furthermore, with conventional autoradiographic techniques, the detection limit for $^{165}$Dy is comparable to that for $^{32}$P, approximately 0.5 dpm per mm$^2$ for an autoradiographic exposure of 12 hours. Assuming that a spot of a substance to be detected occupies 2 mm$^2$, that on average Dy atoms are bound to a molecule to be detected, (e.g., to a protein molecule), and that residual binding of a Dy-containing labeling ligand to the separation matrix is negligible, it can be shown (see below) that the detection limit under these conditions is $3 \times 10^{-19}$ moles (0.3 attomoles). This molar limit corresponds, for example, to approximately $2 \times 10^5$ molecules of a medium-sized protein (with a molecular weight of 50,000 daltons). For comparison, a large proportion of proteins in a single mammalian cell are present in numbers exceeding $1 \times 10^5$ per cell.

Phosphorus has an absorption cross-section of 0.19 Barns and a half-life of $^{32}$P is 14.6 days. A 6 hr irradiation at a flux of $10^{10}$ neut/cm$^2$ would activate phosphorus to approximately $1 \times 10^{-3}$ dpm/nmole. Thus, a 10 nmole, 1 cm$^2$, spot of ATP would not be detectable after such a short, low flux irradiation at this flux. In contrast, manganese ion $^{56}$Mn which binds tightly to phosphate groups has a neutron capture cross-section of 13.4 Barns and a half-life of 2.58 hr. Thus, the Mn nucleus captures neutrons 70-fold more efficiently than the phosphorus nucleus and a 6 hr irradiation takes it through 2.33 half-lives and gives 80% of saturation where the phosphorus nucleus would go through 0.017 of a half-life giving 1.2% of the maximum saturation activity. Thus, if $Mn^{++}$ binds phosphate groups more efficiently than it does the chromatographic matrix, it is possible to visualize phosphate containing compounds with short, low flux irradiations. When one-dimensional PEI chromatograms of the standard adenosine nucleotides are treated with solutions of manganese acetate in methanol as described and irradiated for 6 hr at a flux of $10^{10}$ n/cm$^2$ sec, the 10 nmole spots of ATP, ADP and AMP were detectable in a 12 hr exposure. Re-exposures of the same plates to film the next day showed no spots demonstrating that the signal was due to manganese rather than phosphorus activation.

Autoradiography is typically performed by methods known n the art where the radioactivity in a specimen is detected by producing an image on a photographic film or plate.

The following examples refer to chromatography techniques for preparing chromatograms of nucleotides and electrophoretic techniques for preparing gels containing nucleotides. When such techniques are referred to, they are carried out in the following manner.

For the chromatography technique, standard solutions of adenosine nucleotides or complex mixtures of nucleotides extracted from cells were spotted on polyethylenimine TLC plates, 2 cm from the bottom of the plate in a volume of 20 μl or less of $H_2O$ or 0.2M ammonium bicarbonate, pH 8.0. The plates were then placed in glass distilled methanol for 5 minutes to dehydrate the cellulose layer, then air dried. Ascending chromatography in 0.9M guanidinium hydrochloride pH 6.5 then was carried out to achieve a separation of the nucleotides based on charge. After chromatography, the plates were washed in methanol for 20 minutes to remove salts, then air dried. The backs of the mylar supporting sheets were taped over with Scotch Patch and Repair tape to prevent brittleness in the mylar sheets which would otherwise develop during the high flux irradiation used. The plates were placed in heat-sealed polyethylene bags for irradiation. After irradiation and "cool down", the cellulose layer is removed from each plate by pressing it down on a layer of photomount spray adhesive on cardboard. The mylar backing is peeled off and discarded. Double sided tape can be used in place of spray adhesive. This transfer is necessary because the cellulose layer is held to the mylar sheet by a binder layer of calcium sulfate (gypsum). This gypsum binder contains elements such as antimony and cesium which activate enough upon neutron irradiation to interfere with autoradiographic detection of the samples. The gypsum binder is removed with the mylar.

For the electrophoretic technique, a 3 mm thick horizontal 1% agarose slab gel (15×10 cm) was cast in running buffer composed of 40 mM Tris base, 0.1 mM acid form EDTA adjusted to pH 8.0 with glacial acetic acid. The sample DNA was loaded in a buffer composed of 2.5% ficol, 0.1% SDS, 0.025% xylene cyanol and 0.025% Bromophenol blue. Electrophoresis was carried out at 5 V/cm for the times indicated. After electrophoresis, the gel was removed from the tank and placed on a double layer of fine nylon cloth and two layers of blotting paper and dried down with heat and vacuum on a commercial gel drier. The nylon prevented the dried agarose from adhering to the paper. The dried agarose was removed as a flexible membrane, placed between two stiff polyethylene sheets for protection during handling. The polyethylene sheets were taped together with Scotch Patch and Repair tape and the assembly placed in a heat-sealed polyethylene bag for irradiation.

EXAMPLE

This example illustrates the increased versatility and ease obtained with the "indirect labeling" process of this invention as compared to the prior art "direct labeling" process. The process of this invention is versatile since detection of non-phosphorus compounds can be attained. Ease of conducting the process of this invention is achieved since highly neutron activatable elements requiring only low neutron fluence (neutron flux) can be utilized.

Unlabeled nucleotides (P.L. Biochemicals) were dissolved in $H_2O$ and stored at $-70°$ C. TLC plates were PEI-impregnated cellulose layers bound to mylar sheets (Polygram Cell 300 PEI from Brinkman or Bakerflex PEI cellulose from J. T. Baker Chemical Co.).

Direct Labeling: Neutron-Irradiation and Processing of TLC Plates and Agarose Gels. After TLC, the plates were immersed in glass-distilled $CH_3OH$ (Omnisolve) for 10 min, then air dried. The backs of supporting mylar sheets were taped over with Scotch Patch and Repair tape (3M Co.) to prevent the sheets from becoming brittle after irradiation. The plates were placed into polyethylene bags and irradiated with thermal neutrons within a vertical thimble in the graphite reflector of the Massachusetts Institute of Technology reactor for 96 hours at a flux of $4 \times 10^{12}$ neutrons.sec$^{-1}$.cm$^{-2}$, unless stated otherwise. The samples were "cooled down" for 2 days (longer in some experiments) to allow $^{24}$Na and other short-lived isotopes to decay to levels below detection. Thereafter, irradiated TLC plates were pressed cellulose side down onto a layer of Scotch Photomount Spray adhesive (3M Co.) on a cardboard, and the mylar backing together with the intermediate binding layer was peeled off. Double-sided Scotch tape can be used in place of spray adhesive. Removal of the backing is necessary because it contains trace amounts of metals such as $^{75}$As and $^{133}$Cs, whose neutron activation-produced radiation interferes with detection of phosphorus-containing compounds separated by TLC.

Agarose gels after DNA electrophoresis were washed in $H_2O$, then placed onto several layers of Whatman 3MM paper and dried under vacuum at 60° C. Dried agarose was peeled off the backing, placed between two stiff polyethylene sheets and irradiated as described above.

Indirect Labeling.

(i) Nucleotides. After TLC, the PEI plate (Brinkman) was immersed in 0.3 mM manganese acetate in glass-distilled $CH_3OH$ for 10 min, unless stated otherwise, then immersed for an additional 10 min in $CH_3OH$ alone and thereafter irradiated for 6 hours at $10^{10}$ neutrons.sec$^{-1}$.cm$^{-2}$. Two hours after irradiation, the chromatogram (with mylar backing still attached) was placed face down onto Kodak X-Omat AR film and exposed for 12 hours at $-70°$ C.

(ii) Proteins. After separation of a standard mixture of proteins on lithium dodecyl sulfate-containing 12% polyacrylamide mini-gels (0.75 mm thick, 8×10 cm, Hoefer), the gels were washed for 1 hour in 50% $CH_3OH$ in $H_2O$, followed by washing in 10% $CH_3COOH$, 25% $CH_3OH$ for 1 hour and incubation for 20 min in the same solvent with a mixture of 30 mM bathophenantroline disulfonate (BPS, Sigma) and either 1 mM EuCl$_3$ or 1 mM DyCl$_3$ (Aldrich). BPS, an aromatic protein-binding dye, reacts to complex the Eu or Dy ions. The gels were destained by washing for 30 min in several changes of 10% CH$_3$COOH, 25% CH$_3$COOH. Dried gels were irradiated for 15 min at $1 \times 10^{13}$ neutrons.cm$^{-1}$.sec$^{-2}$ and exposed for autoradiography as described below.

Autoradiography. Irradiated and "cooled down" samples were wrapped in Saran Wrap and exposed at $-70°$ C. with Kodak X-Omat AR film, either with or without intensifying screens (Lightning Plus, Dupont). Filters (either a 0.5 mm thick aluminum foil or 0.2 mm thick mylar sheets) were placed between the sample and both the film and intensifying screens to reduce interferring radiation due to traces of neutron-activated isotopes within separation support materials.

Post-Separation Detection of Nucleotides by Direct-Labeling Neutron Activation. To determine the sensitivity of the direct-labeling method for $^{31}$P, a ten-fold dilution series of ATP was spotted onto a TLC plate and irradiated with thermal neutrons as described above to convert the $^{31}$P of ATP into $^{32}$P. The lowest amount of ATP detected after 12 hours of autoradiographic exposure was approximately 5 pmoles in a spot about 2 mm in diameter. Since each ATP molecule contains three phosphorus atoms, the detection limit under conditions used is approximately 5 pmoles of $^{31}$P per mm$^2$. The specific radioactivity of ATP obtained in this direct-labeling procedure is approximately $13 \times 10^3$ cpm/g or 2.7 mCi/mmole which is comparable to specific radioactivities of ATP produced by metabolic labeling of mammalian cells in culture with $^{32}$P, but only $10^{-5}$% of the theoretical limit (27,000 Ci/mmole).

Under conditions used, 0.1 nmoles of ADP and ATP are detectable readily after 6 hours of autoradiographic exposure, and the relative intensities of spots are directly proportional to the number of phosphorus atoms present per nucleotide. Total intracellular nucleotides resolved either in a short unidimensional TLC run or in two-dimensional fractionations could also be readily visualized by the direct-labeling neutron activation. The background noise due to the presence of traces of highly activatable elements in PEI cellulose layers was approximately constant for different lots of a given brand of PEI cellulose plates but varied greatly between different brands, with the plates from Brinkman consistently yielding the lowest background.

Indirect-Labeling Neutron Activation: Post-Separation Detection of Nucleotides. Direct post-separation labeling of phosphorus-containing compounds by neutron activation (see above) required irradiation at high neutron fluxes ($4 \times 10^{12}$ neutrons sec$^{-1}$.cm$^{-2}$) for relatively long periods of time (96 hours). This is largely due to a relatively low neutron capture cross-section of $^{31}$P (0.19 Barns). On the other hand, manganese ($^{55}$Mn) has a 74-fold higher neutron capture cross-section, 13.4 Barns, and $^{56}$Mn, the product of neutron irradiation of $^{55}$Mn, decays with a half-life of only 2.6 hours. Thus, if Mn$^{2+}$ ions bind to separated nucleotides more efficiently than they bind to chromatographic support matrix, it is possible to detect these compounds with shorter, lower-flux irradiations than those required in the direct labeling method. Indeed, when one-dimensional PEI chromatograms of adenosine nucleotides were treated with manganese acetate solution, and thereafter irradiated for 6 hours at $10^{10}$ neutrons.sec$^{-1}$.cm$^{-2}$, the spots of ATP (3 nmoles), ADP (10 nmoles) and AMP (2 nmoles) were detectable demonstrating that the autoradiographic signal was due to $^{56}$Mn rather than $^{32}$P.

Post-Separation Detection of Proteins via Indirect-Labeling Neutron Activation. As a protein-binding, neutron-activatable ligand we chose complexes of an aromatic dye bathophenantroline disulfonate (BPS) with either europium (Eu$^{3+}$) pr dysprosium (Dy$^{3+}$) ions. $^{151}$Eu and $^{164}$Dy are among the most highly activatable elements, with activation cross-sections of 3000 and 2600 Barns, respectively. BPS (in a complex with Fe$^{2+}$ ions) has previously been shown to bind to proteins and has been suggested as a general protein stain, Graham et al, Anal. Biochem. 88: 434–441 (1978). Other neutron-activatable elements may also be useful for the indirect-labeling approach as has been stated on page 6.

A 12% polyacrylamide-LiDodSO$_4$ gel containing separated standard proteins was incubated with the Dy$^{3+}$/BPS complex, washed to remove the free complex and thereafter irradiated with neutrons for 15 minutes at a flux of $1 \times 10^{13}$ neutrons.cm$^{-2}$. sec$^{-1}$. Autoradiography of the gel 29 hours later showed that this procedure allows detection of separated proteins down to less than 0.1 μg of protein per a 0.5 cm wide protein band. Analogous results were obtained using the Eu$^{3+}$/BPS complex. Inasmuch as the background noise in autoradiographic patterns decayed with virtually the same half-life as the corresponding signal (T$_{\frac{1}{2}}$ about 9 hours), we conclude that most of the background noise is due to incomplete removal of dysprosium and europium not bound to proteins. It is also clear that the sensitivity of protein detection using the above-activatable ligands is limited largely by the background noise, since the signal itself could be readily increased by orders of magnitude using longer than 15-minute irradiation times, higher neutron fluxes and longer autoradiographic exposures.

The major new result in this example is the demonstration of feasibility of the indirect-labeling approach to post-separation detection of specific compounds via neutron activation. In the indirect-labeling method, separated compounds of interest are selectively bound to highly neutron-activatable elements such as $^{55}$Mn, $^{151}$Eu or $^{164}$Dy. These elements are then made radioactive by neutron irradiation. The indirect-labeling method can, in principle, vastly exceed sensitivities achievable in most direct-labeling settings. The sensitivity of detection in neutron activation analysis depends in particular on the cross-section of the element to be activated and on the half-life of the corresponding unstable isotope. Specifically, for the w grams of an isotopically pure element with the atomic weight of A $$S = 0.6025 \frac{w\sigma f}{A} (1 - e^{-\lambda t})$$

where S is the induced radioactivity (in disintegrations per second) after an irradiation time t (in seconds), $\sigma$ is the activation cross-section of the element (in Barns; 1 Barn = $1 \times 10^{-24}$ cm$^2$). f is the neutron flux (in neutrons cm$^{-2}$.sec$^{-1}$) and $\lambda$ is the decay constant $$(\lambda = \frac{0.693}{T}$$

where T is the half-life of activated isotopes in seconds).

For $^{151}$Eu as an indirect-labeling ligand and for a readily achievable neutron flux of $5 \times 10^{13}$ neutrons.cm$^{-2}$.sec$^{-1}$, application of the above formula shows that the specific radioactivity obtained after irradiating $^{151}$Eu for one half-life of $^{152}$Eu (9.2 hours) is approximately $2.8 \times 10^9$ disintegrations min$^{-1}\cdot\mu$g$^{-1}$ (dpm/$\mu$g). Longer irradiations would produce not more than a 2-fold increase in specific radioactivity. Furthermore, with conventional autoradiographic techniques, the detection limit for $^{151}$Eu is comparable to that for $^{32}$P, and is approximately 0.5 dpm per mm$^2$ after 12 hours of autoradiographic exposure. Assuming that a spot of a substance to be detected occupies 2 mm$^2$, that on average five $^{151}$Eu atoms are bound to a molecule to be detected (e.g., to a protein molecule) and that nonspecific binding of the labeling ligand is negligible, application of the above formula yields a detection n limit of approximately $3 \times 10^{-19}$ moles (0.3 attomoles).

Thus, it is clear that the sensitivity of detection achieved in the initial applications of the indirect-labeling method described in the above example is limited almost entirely by the background noise due to unbound ligands. Future refinements of the indirect-labeling method may employ covalent attachment of neutron-activatable ligands to separated compounds of interest, to facilitate subsequent complete removal of unbound ligands. Achievement of no more than 10% of the above theoretical sensitivity of detection by the indirect-labeling method should allow, among other things, post-separation detection and quantitation of medium-abundance proteins from a single mammalian cell.

We claim:

1. A method for detecting an organic molecular species of interest in a substrate composition which comprises separating said substrate composition utilizing a support material or support matrix formed of elements which when irradiated have a half life less than both phosphorous and an element having a large neutron adsorption cross-section to isolate the organic molecular species of interest, binding said element having a large neutron adsorption cross-section which is neutron-activatable to form a radioactive isotope to said organic molecular species of interest, said separating step being either prior to or subsequent to said binding step, activating said bound element with neutrons after said separating step to form a radioactive isotope and detecting the presence of said organic molecular species by detecting radiation emitted by said radioactive isotope.

2. The method of claim 1 wherein said separation step precedes said separation step.

3. The method of claim 1 wherein said binding step precedes said separation step.

4. The method of claim 1 or 2 wherein said element is bound directly to said organic molecular species.

5. The method of claim 1 or 2 wherein said element is bound to said organic molecular species through a ligand which is specifically reactive with said organic molecular species.

6. A method according to claim 1 or 2 wherein said separation step comprises chromatography or electrophoresis.

7. A method according to claim 1 or 2 wherein said organic molecular species of interest is a nucleotide or a polynucleotide.

8. A method according to claim 1 or 2 wherein said element is selected from the group consisting of a transition metal, a lanthanide and an actinide.

9. A method according to claim 4 wherein said molecular species is a nucleotide.

10. The method of any one of claims 1, 2 or 3 wherein said element is dysprosium.

11. The method of any one of claims 1, 2 or 3 wherein said element is manganese.

12. The method of any one of claims 1, 2 or 3 wherein said element is europium.

13. The method of claim 4 wherein said element is dysprosium.

14. The method of claim 4 wherein said element is manganese.

15. The method of claim 4 wherein said element is europium.

* * * * *